United States Patent
Sestok, IV et al.

(10) Patent No.: US 9,902,068 B1
(45) Date of Patent: Feb. 27, 2018

(54) IMPEDANCE SIGNATURE ANALYZER TO CONTROL AUTOMATED ACTIONS

(71) Applicants: TEXAS INSTRUMENTS INCORPORATED, Dallas, TX (US); TEXAS INSTRUMENTS DEUTSCHLAND GMBH, Freising (DE)

(72) Inventors: Charles Kasimer Sestok, IV, Dallas, TX (US); Alan Henry Leek, Frisco, TX (US); Bjoern Oliver Eversmann, Bavaria (DE); Matthew Justin Calvo, Gainesville, FL (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/394,279

(22) Filed: Dec. 29, 2016

(51) Int. Cl.
```
G01N 27/02      (2006.01)
B25J 9/16       (2006.01)
B65G 47/90      (2006.01)
A47L 9/28       (2006.01)
```

(52) U.S. Cl.
CPC ........... *B25J 9/1694* (2013.01); *A47L 9/2826* (2013.01); *B65G 47/905* (2013.01); *G01N 27/02* (2013.01)

(58) Field of Classification Search
CPC ...................................................... G01N 27/02
See application file for complete search history.

(56) References Cited

U.S. PATENT DOCUMENTS

| | | | | |
|---|---|---|---|---|
| 5,501,766 A * | 3/1996 | Barbee | ................... | G01N 27/02 156/345.16 |
| 6,414,497 B1 * | 7/2002 | Sovik | ....................... | G01N 9/00 324/663 |
| 6,784,672 B2 * | 8/2004 | Steele | ................... | G01N 27/02 324/663 |
| 6,803,771 B2 * | 10/2004 | Sovik | ....................... | G01N 9/00 324/654 |
| 8,547,110 B2 * | 10/2013 | Kesil | ................... | G01N 27/023 324/633 |
| 9,341,687 B2 * | 5/2016 | Donnangelo | ........... | G01N 22/00 |
| 9,389,260 B2 * | 7/2016 | Potyrailo | ................ | G01R 27/28 |
| 9,546,004 B1 * | 1/2017 | Safai | ...................... | B64D 45/00 |
| 2016/0187520 A1 * | 6/2016 | Widmer | ................. | G01V 3/101 324/227 |
| 2016/0274060 A1 * | 9/2016 | Denenberg | ......... | G01N 27/9046 |

* cited by examiner

*Primary Examiner* — Thomas Randazzo
(74) *Attorney, Agent, or Firm* — Michael A. Davis, Jr.; Charles A. Brill; Frank D. Cimino

(57) ABSTRACT

A system includes a controller to provide at least one control output to an automated system in response to a control command received at a control input of the controller. The control output controls the operation of the automated system based on the control command. A signature analyzer generates the control command to the controller and receives an impedance signature related to a property of a material or object encountered by the automated system. The signature analyzer compares the impedance signature to at least one comparison signature to determine the property of the material or object. The signature analyzer adjusts the control command to the controller to control the operation of the automated system based on the determined property.

20 Claims, 8 Drawing Sheets

IMPEDANCE SIGNATURE ANALYZER TO CONTROL AUTOMATED ACTIONS

TECHNICAL FIELD

This disclosure relates to automation systems and circuits and, more particularly, to a system and method to control automated actions based on an impedance signature that describes a property of a material or object.

BACKGROUND

Automation or automatic control includes the use of various control systems for operating equipment such as machinery, processes in factories, inventory management processes and network switching systems, for example. This control can include steering, guidance, and stabilization of vehicles such as ships, aircraft and other applications and vehicles with minimal or reduced human intervention. Some processes have been completely automated as witnessed by newer applications including driverless vehicles, drones, and factory/household robotics, for example. Automation has been achieved by various supporting technologies to the control systems including mechanical, hydraulic, pneumatic, electrical, electronic devices and computers, often in combination. Complicated systems, such as modern factory controls, airplanes and ships typically use all these combined techniques.

Many of these control systems have fixed parameters for guiding operations of the systems. These may include control programs that respond to one or more inputs to the control system. Based on the inputs, various control decisions can be made which affect further automated actions of the system. Although the inputs determine a limited set of operations for the controller, the inputs often do not provide any information as to the quality or types of materials encountered by the system. As such, some control situations can be compromised if this type of information is not suitably processed by the control system.

SUMMARY

This disclosure relates to a system and method to control automated actions based on an impedance signature that describes a property of a material or object. In one example, a system includes a controller to provide at least one control output to an automated system in response to a control command received at a control input of the controller. The control output controls the operation of the automated system based on the control command. A signature analyzer generates the control command to the controller and receives an impedance signature related to a property of a material or object encountered by the automated system. The signature analyzer compares the impedance signature to at least one comparison signature to determine the property of the material or object. The signature analyzer adjusts the control command to the controller to control the operation of the automated system based on the determined property.

In another example, a circuit includes an impedance sensor that includes at least two electrodes that are excited via an alternating current (AC) voltage over a range of frequencies. The impedance sensor generates an impedance signature in relation to a material or object in proximity to the sensor. A classification logic circuit compares the impedance signature from the impedance sensor to at least one comparison signature to determine a property of the material or object. A signature analyzer processor generates a control command to control an automated system. The signature analyzer processor adjusts the control command to control the operation of the automated system based on the determined property of the material or object by the classification logic.

In yet another example, a method includes providing an alternating current (AC) voltage over a range of frequencies to at least one impedance sensor to receive an impedance signature that relates to a material or object in proximity to the sensor. The method includes comparing the impedance signature from the impedance sensor to at least one comparison signature to determine a property of the material or object. The method includes adjusting a control command to control the operation of an automated system based on the determined property of the material or object.

DETAILED DESCRIPTION

This disclosure relates to a system and method to control automated actions based on an impedance signature that describes a property of a material or object. An impedance sensor is provided that includes at least two electrodes that are excited via an alternating current (AC) voltage over a range of frequencies. The impedance sensor generates an impedance signature in relation to a material or object in proximity to the sensor. The impedance sensor can be placed on autonomous systems such as robots to determine if autonomous actions of the system should continue, be avoided, or adjusted, for example (e.g., alter gripping force based on signature). Classification logic compares the impedance signature from the impedance sensor to at least one comparison signature to determine a property of the material or object. The property can relate to a type of material or object encountered or related to a particular quality such as liquid, sold, hardness, and so forth. The comparison signature (or signatures) can be stored in a memory or database and represent materials or object signatures that have been previously classified. A signature analyzer generates a control command to control an automated system based on the comparison of the impedance signature and the comparison signature.

The signature analyzer can adjust the control command to control the operation of the automated system based on the determined property of the material or object by the classification logic. For example, the signature analyzer can send the control command to a controller which in turn can affect the operations of the automated system. In a vacuum robot example for the automated system, the robot can be controlled via the controller to vacuum a material or avoid the material based on detected properties of the material. If a material is detected that may be harmful to the robot, the robot can be instructed to bypass the material.

Other applications can include pick and place systems where actions of the system (e.g., gripping force applied to an object) can be adjusted based on an impedance signature detected for the object. Other applications include inventory management systems such as drones or inventory selection robots that can decide whether or not a potential object is to be selected from inventory based on the impedance signature of the object. In some examples, one or more other sensors can be provided which operate in conjunction with the impedance sensor to further control actions of the automated system and facilitate safety in the system. For instance, if an object is first sensed by an optical sensor, the impedance sensor can then be moved in proximity to the object to further determine if any other automated actions should occur (e.g., grip object or avoid object). In this manner, a secondary inspection is provided by multiple sensor processing to facilitate operating the automated system in a substantially safe manner.

Figure 1:
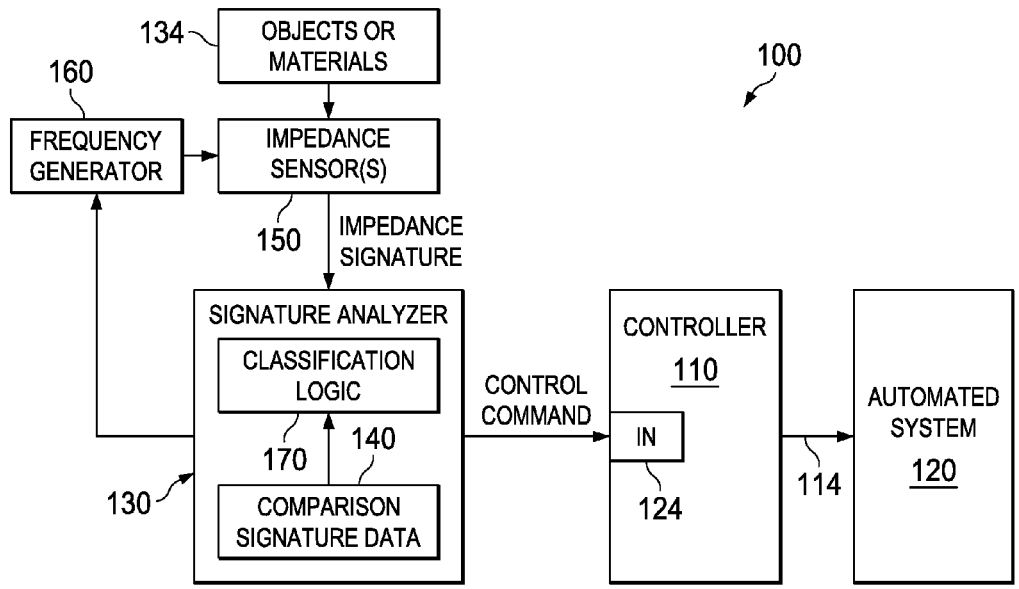
FIG. 1 illustrates a schematic block diagram of an example system to control automated actions based on an impedance signature that describes a property of a material or object.

FIG. 1 illustrates an example system 100 to control automated actions based on an impedance signature that describes a property of a material or object. The system 100 includes a controller 110 to provide at least one control output 114 to an automated system 120 in response to a control command received at a control input 124 of the controller. The control output 114 controls the operation of the automated system 120 based on the control command. A signature analyzer 130 generates the control command to the controller 120 and receives an impedance signature related to a property of a material or object 134 encountered by the automated system 120. As used herein, the term property refers to a type or quality of the material or object, where type relates to the differences between objects/materials such as dirt, food, debris, paper, insulator, plastic, stone, sand, and so forth. Quality refers to difference in structure of the material/object such as fragile, hard, flexible, and so forth. The signature analyzer 130 compares the impedance signature to at least one comparison signature from a comparison signature data file 140 to determine the property of the material or object 134. The signature analyzer 130 adjusts the control command to the controller 110 to control the operation of the automated system 120 based on the determined property.

An impedance sensor 150 is operatively coupled to the signature analyzer 130 to generate the impedance signature. The impedance sensor 150 includes at least two electrodes that are excited via an alternating current (AC) voltage from frequency generator 160. The AC voltage is varied over a range of frequencies by the signature analyzer 130 and frequency generator 160 to generate the impedance signature. As will be illustrated and described below with respect to FIGS. 8-10, the impedance sensor 150 can include at least two electrodes that are positioned on a similar sensing plane or positioned on a different sensing plane with respect to each other to sense the material or object 134 encountered by the automated system. The impedance signature includes at least one of a magnitude component and a phase component that is analyzed over the range of frequencies by the signature analyzer 130 to determine the property of the material or object 134.

At least one other sensor (see e.g., FIG. 2) can be provided in addition to the impedance sensor 150 to detect the presence of the material or object 134 encountered by the automated system. After the object is detected, the impedance signature can then be gathered from the detected object to determine if the object should be further processed or avoided by the automated system 120. By using multiple sensors, additional feedback is provided to the controller 110 to first perform a rudimentary check for object presence followed by a more detailed analysis with respect to the impedance signature generated by the impedance sensor 150. Such multi-sensor cooperation provides an additional level of checking in the system 100 to facilitate safety in the system to mitigate the automated system 120 from performing an action before checking the impedance signature.

The signature analyzer 130 can include a classification logic circuit 170 to perform the comparison between the impedance signature and the comparison signature stored at 140. The classification logic circuit 170 can include at least one of an analog comparator, a digital comparator (e.g., following an ADC), or a classifier to compare the impedance signature to the comparison signature to determine the property of the material or object 134. As used herein, the term classifier can include substantially and type of artificial intelligence that uses trained statistical reasoning to analyze the impedance signature. These can include support vector machines, for example, or other types of learning such as a neural network, for example. Also, as used herein, the term circuit can include a collection of active and/or passive elements that perform a circuit function such as an analog circuit or control circuit, for example. Additionally or alternatively, the term circuit can include an integrated circuit (IC) where all and/or some of the circuit elements are fabricated on a common substrate (e.g., semiconductor substrate), for example. Other aspects of the system 100 including examples of automated systems and control are illustrated and described below with respect to FIG. 2.

Figure 2:
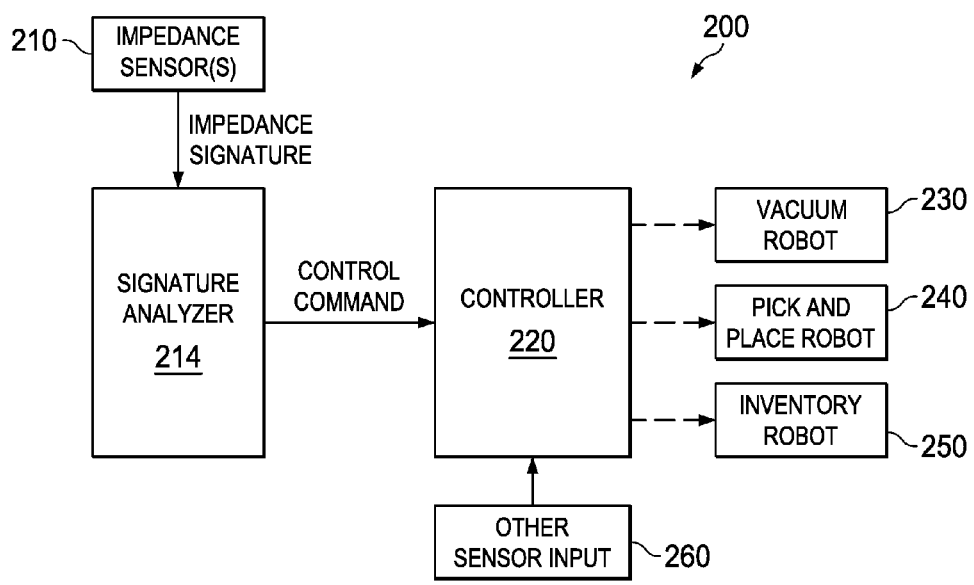
FIG. 2 illustrates a schematic block diagram of an example system to control automated actions of example automated systems based on an impedance signature that describes a property of a material or object.

FIG. 2 illustrates an example system 200 to control automated actions of example automated systems based on an impedance signature that describes a property of a material or object. As shown, the system 200 can include at least one impedance sensor 210 the provides an impedance signature to a signature analyzer 214 that in turn provides a control command to a controller 220 based off an analysis of the signature as previously described. In this example, the controller 220 is shown interacting with three examples of automated systems although various other types of these systems are possible. In one example, the controller can include a vacuum robot 230 that receives the control output from the controller 220 in response to the control command from the signature analyzer 214. The vacuum robot 230 collects material via vacuum forces or bypasses the material based on the determined property of the material and the control command from the signature analyzer 214.

The material includes solid or liquid materials that are collected or bypassed by the vacuum robot 230 and the control command can be adjusted by the signature analyzer 214 based on a type of flooring material that is in contact with the solid or liquid materials. For example, one impedance signature can be generated for the material or object to be picked up by the vacuum robot 230 and another impedance signature can be gathered from the floor where the material or object is encountered. Based on a signature analysis of the material/object and the associated flooring material in which it resides, the signature analyzer 214 can adjust the control command to controller 220 based on the analysis. For example, on some types of floors no vacuuming is to occur, and on other types of floors, only liquids are to be vacuumed leaving any solid material/objects encountered.

Prior vacuum robots 230 can run over spills and spread the spills over the area to be cleaned. Basic capacitive sensors cannot determine the type of material, whether it is dirt or a spill that should not be spread, for example. The system 200 utilizes impedance signature spectroscopy/analysis to more accurately classify the material and determine whether it is suitable for the robot to continue cleaning. The system 200 can also use the impedance spectra as a fingerprint of the flooring material in each part of the house of factory, for example. Thus, it can be used to detect changes in impedance or to select only certain areas of a given area for cleaning. Also, it can be used to detect obstacles such as electrical cords on the floor or furniture, for example. This can include robotic cleaning program adjustment for surfaces such as carpet, wood, linoleum, tiles, and stone floor, for example. Spill detection ranges for the impedance sensor 210 can be in proximity ranges of about 0.0 cm to about 4.0 cm, for example. The vacuum robot 230 can provide spill detection from speeds of about 0.3 m/s to about 1.0 m/s, for example.

In another automated system example, the controller 240 can control a pick and place robot 240 that receives the control output from the controller in response to the control command from the signature analyzer 214. The pick and place robot 240 can manipulate the object based on the determined property of the object and the control command from the signature analyzer. For example, the determined property of the object can relate to the hardness of the object, where the signature analyzer 214 adjusts to the control command to control an amount of force applied by the pick and place robot to the object (e.g., force grip adjusted smaller for a signature relating to an egg versus a signature relating to a hard solid object).

In yet another automated example, an inventory selection robot 250 can receive the control output from the controller 220 in response to the control command to the signature analyzer 214. The inventory selection robot 250 retrieves the object based on the determined property of the object and the control command from the signature analyzer. As used herein, an inventory selection robot can be a guided vehicle along a track or wheels that is guided to an inventory location to select inventory from the given location. Other examples include drones which fly to a location to select inventory from the location. As shown, one or more other sensors such as optical or acoustical sensors can be provided to supplement the information received from the impedance sensor 210. For example, multiphase analysis can include object detection via the sensor 260 where further analysis is conducted by analyzing the impedance signature from the detected object to provide an additional level of certainty before proceeding with an automated action.

Figure 3:
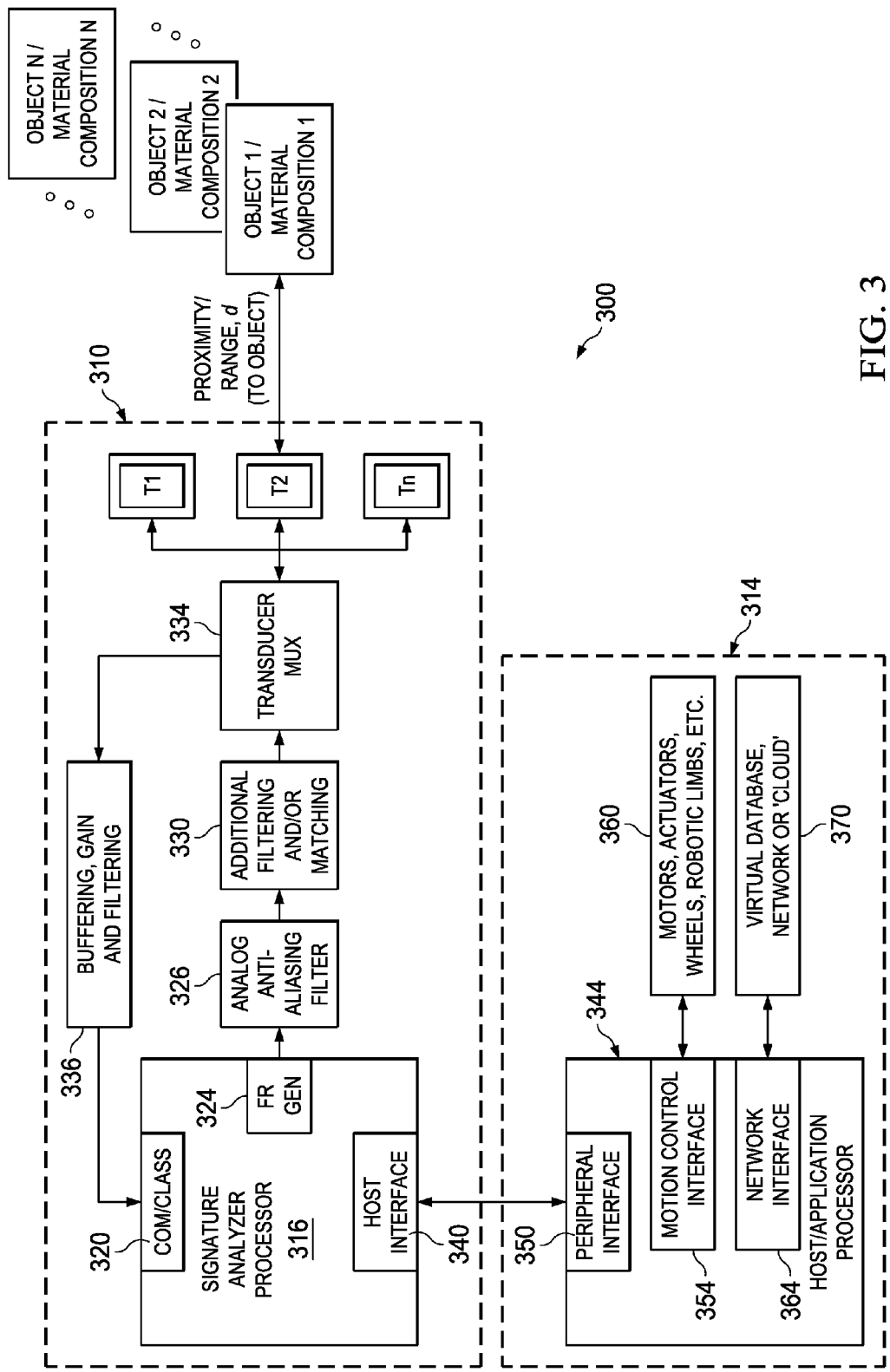
FIG. 3 illustrates an example of a circuit and system to control automated actions based on an impedance signature that describes a property of a material or object.

FIG. 3 illustrates an example of a circuit 310 and system 314 to control automated actions based on an impedance signature that describes a property of a material or object. The circuit 314 includes a signature analyzer processor 316 that analyzes an impedance signature via a comparator or classifier shown at 320. The signature analyzer 316 interacts with a frequency generator 324 (e.g., pulse width modulator, RF generator). Output from the frequency generator can be passed through an anti-aliasing filter 326 which can be further filtered at 330. Output from filter 330 can drive a transducer multiplexor which can drive one through N transducers shown as T1 through Tn, where N is a positive integer. Each of the transducers can analyze one or more objects/materials 1 though N when such objects/materials are within a given proximity or range to the transducers. In some cases, the transducers can be attached to a robot (e.g., robot vehicle or robotic arm) and moved in proximity toward the object/materials when the robot moves. Output from the transducers is fed back to the signature analyzer processor 316 via the multiplexor 334 and a buffer/gain/filter stage 336.

The signature analyzer 316 can interface via a host interface 340 with an application processor 344 acting as a controller via a peripheral interface 350. A motion control interface 354 can be provided to send control commands to robotic components such as motors, actuators, wheels, robotic limbs, and so forth at 360. A network interface 364 may also be provided to gather other control information from a virtual database or cloud shown at 370.

The circuit 310 can operate as an embedded impedance spectroscopy and material discerning proximity sensing front end and can operate singly or by augmenting other sensors in autonomous robotic systems. Such a sensing system can facilitate material and obstacle detection for the benefit of engagement/avoidance decisions in a given operational environment, for example for an autonomous robotic floor vacuum cleaner as previously described. In the example of the robotic vacuum cleaner, the system can take baseline material readings from around a building/household in order to map flooring types, which can then be used as a basis of comparison for new material types introduced that the system may encounter at a later time. Such a sensing system can also facilitate measurements taken by the autonomous system for a determination about quality/validity/fragility of materials engaged, for example a robotic arm for movement of goods in manufacturing.

Multiple sensors can be arranged on the autonomous systems to, for example, introduce benefits of spatial processing. A database of material readings/signature data which can implement the use of large databases, which may warrant connection of the system to a network, or the cloud, via hardware such as a networked application/host processor in order to look up the material signature detected. Transducers shown are example of capacitive fringing field variety, but the transducer can also include coil antennas, dipoles and/or other radiating structures. Other example implementations may include different hardware or more instantiations of the hardware in the system (e.g., multiple front-ends for different tuning). The signature analyzer processor 316 and host processor 344 configuration is a typical example, but these functions can also be combined into, for example, a single integrated circuit.

Figure 4:
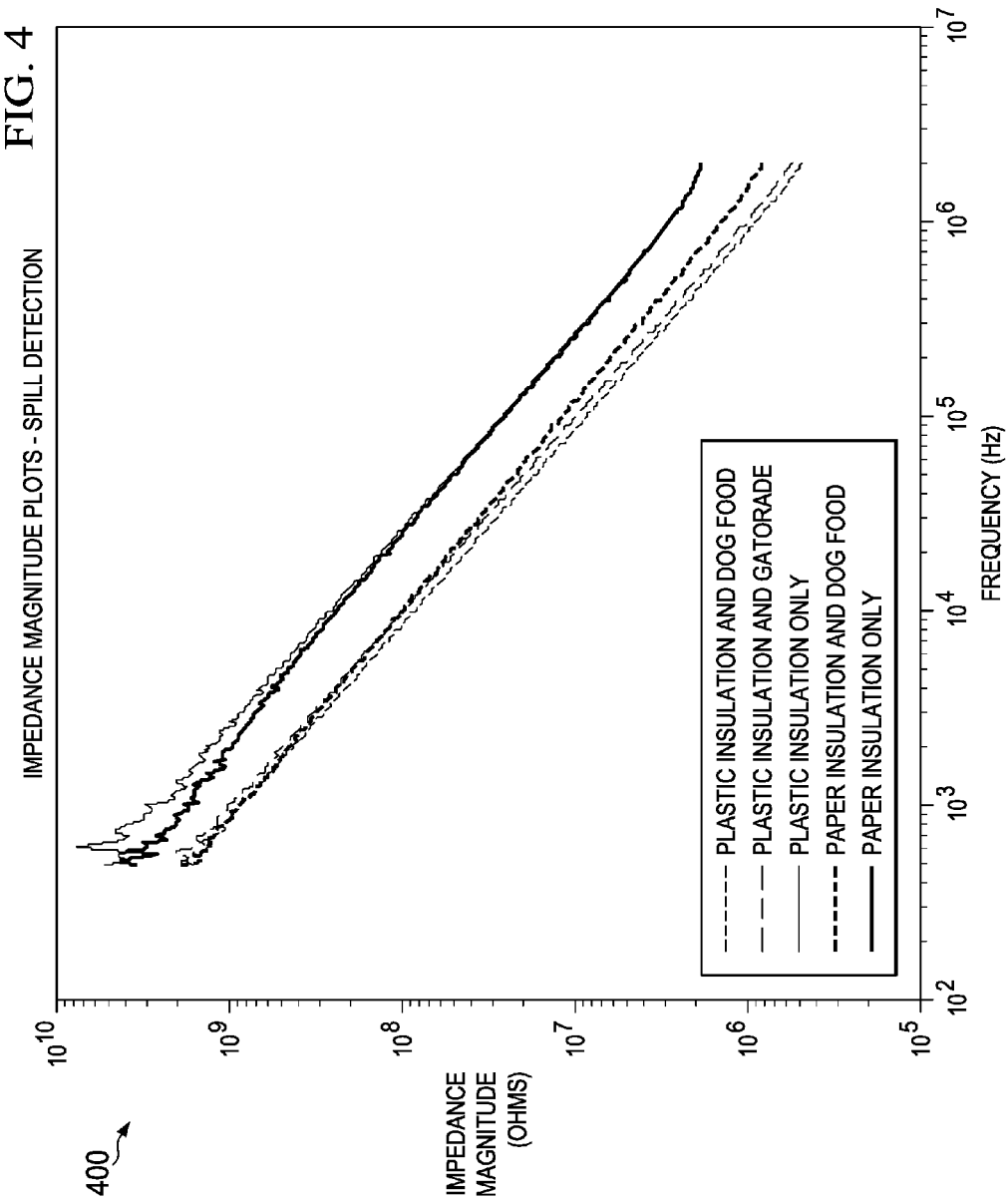
FIG. 4 illustrates an example diagram depicting a magnitude plot for example impedance signatures relating to liquids and solids.

FIG. 4 illustrates an example diagram 400 depicting a magnitude plot for example impedance signatures relating to liquids and solids. The diagram 400 represents frequency along the horizontal axis with respect to impedance magnitude in ohms on the vertical axis. The example signatures include a signature for plastic insulation and dog food, plastic insulation and a liquid (e.g., Gatorade), plastic insulation by itself, paper insulation and dog food, and paper insulation by itself. Other signatures are possible.

Figure 5:
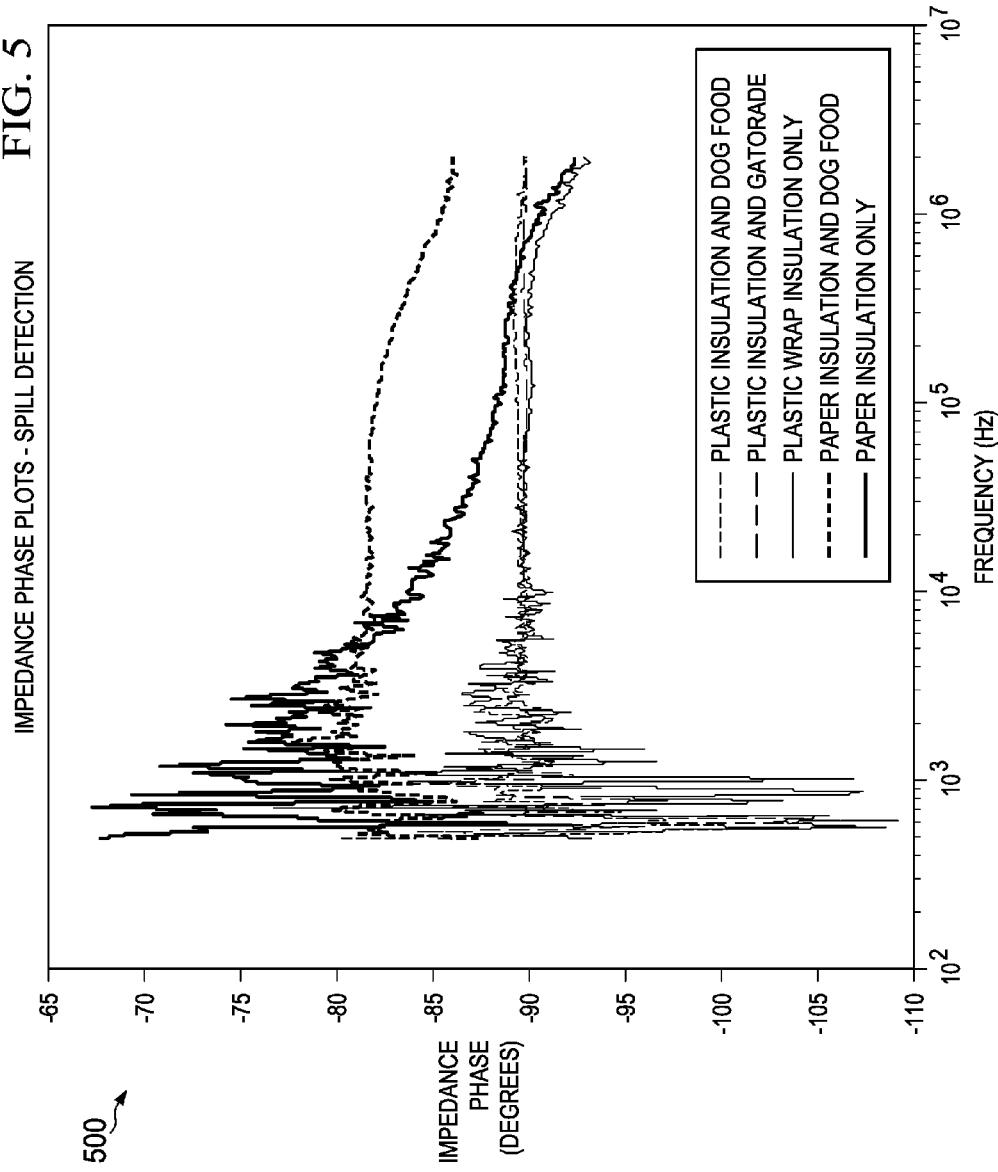
FIG. 5 illustrates an example diagram depicting a phase plot for example impedance signatures relating to liquids and solid.

FIG. 5 illustrates an example diagram depicting a phase plot 500 for example impedance signatures relating to liquids and solid. The diagram 500 represents frequency along the horizontal axis with respect to impedance phase represented along the vertical axis. Phase can be measured as a time delay between when a frequency is applied to the sensor and with respect to a phase shift of a received signal at the signature analyzer. Similar to the magnitude plots of FIG. 400, the example signatures on the plot 500 include a signature for plastic insulation and dog food, plastic insulation and a liquid (e.g., Gatorade), plastic insulation by itself, paper insulation and dog food, and paper insulation by itself. In some cases, magnitude signatures can be analyzed. In other cases, phase signatures can be analyzed. In yet other cases, both magnitude and phase signatures can be analyzed to determine a respective control command.

Figure 6:
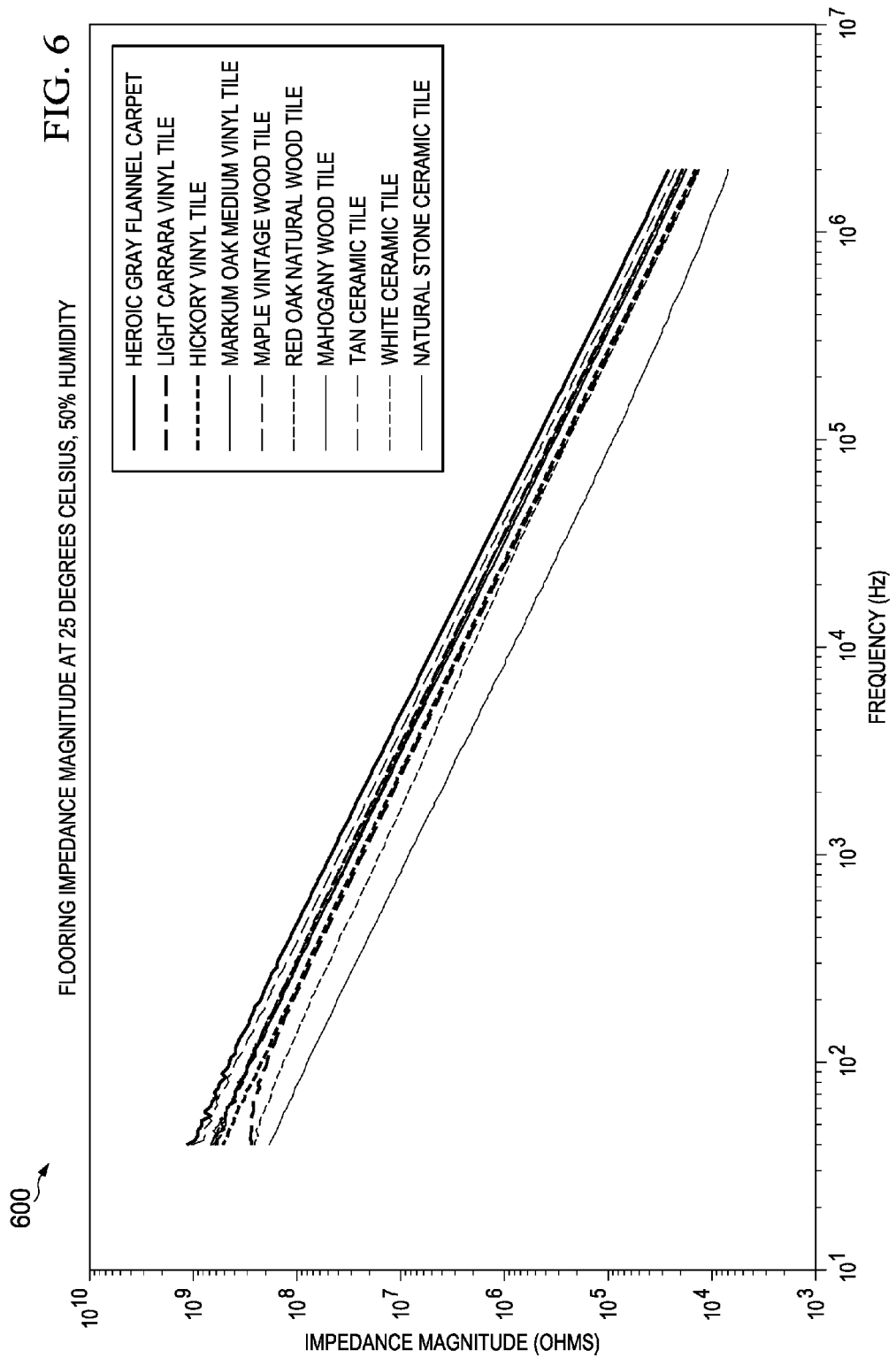
FIG. 6 illustrates an example diagram depicting a magnitude plot for example impedance signatures relating to flooring materials.

FIG. 6 illustrates an example diagram 600 depicting a magnitude plot for example impedance signatures relating to flooring materials. The diagram 600 represents frequency along the horizontal axis with respect to impedance magnitude in ohms on the vertical axis. In this example, flooring material signatures are depicted and include carpet, light vinyl tile, hickory vinyl tile, oak vinyl tile, maple wood tile, red oak wood tile, mahogany wood tile, tan ceramic tile, white ceramic tile, and natural stone tile, for example. Other flooring magnitude signatures are possible.

Figure 7:
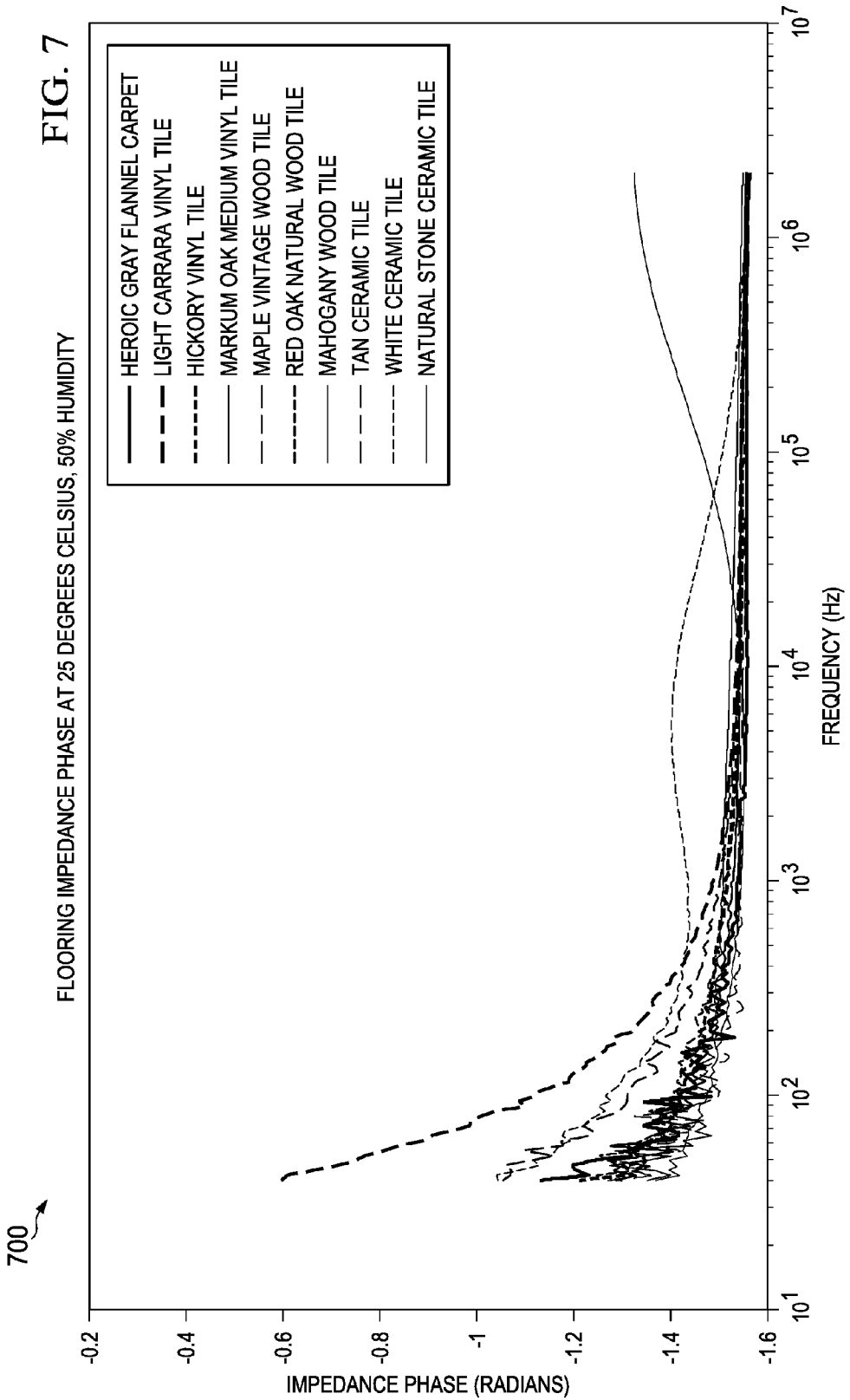
FIG. 7 illustrates an example diagram depicting a phase plot for example impedance signatures relating to flooring materials.

FIG. 7 illustrates an example diagram depicting a phase plot for example impedance signatures relating to flooring materials. The diagram 700 represents frequency along the horizontal axis with respect to impedance phase represented along the vertical axis. Similar to the flooring example signatures of FIG. 6, flooring material signatures with respect to phase include carpet, light vinyl tile, hickory vinyl tile, oak vinyl tile, maple wood tile, red oak wood tile, mahogany wood tile, tan ceramic tile, white ceramic tile, and natural stone tile, for example. Other flooring phase signatures are possible.

Figure 8:
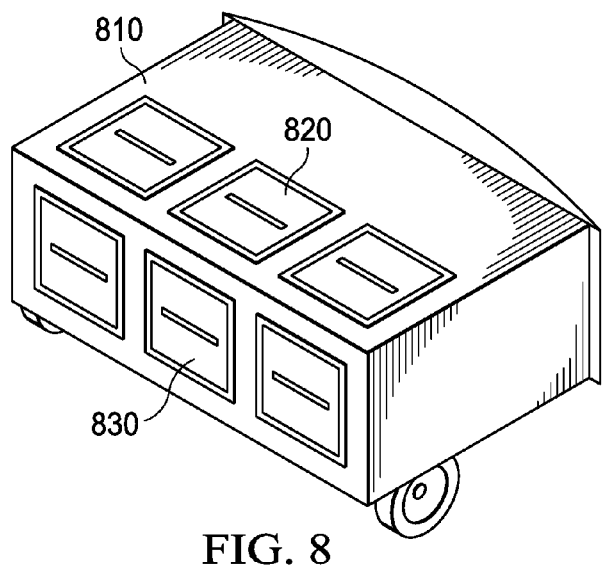
FIGS. 8 though 10 illustrate example electrode configurations for an impedance sensor.
Figure 9:
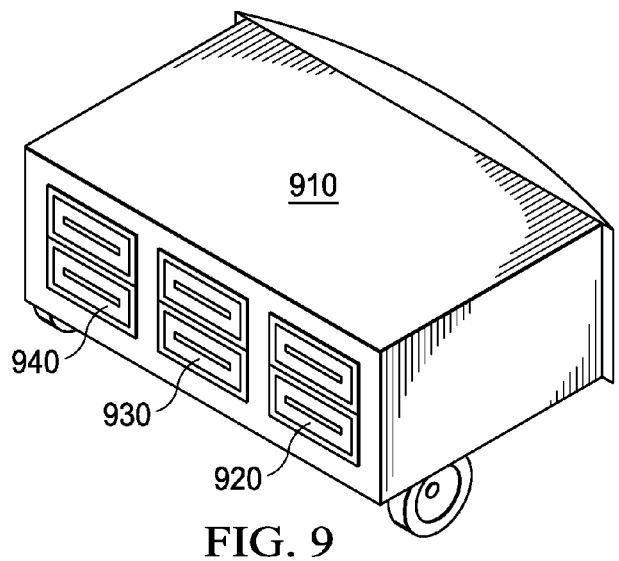
Figure 10:
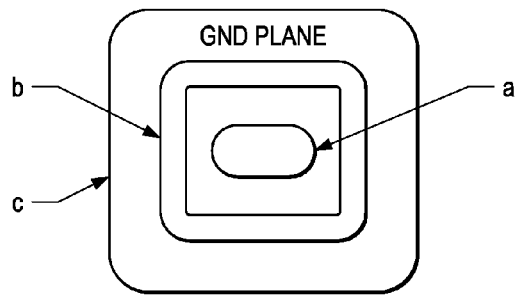

FIGS. 8 though 10 illustrate example electrode configurations for an impedance sensor. With respect to FIG. 8, single electrodes of an impedance sensor are placed on two different planes of a robot 810. For example, an electrode at 820 on a top plane can operate with an electrode 830 on a front plane of the robot 820. Although not shown, electrodes could also be place beneath the robot 810 on a bottom plane which could also interact with the electrodes of the top plane or the front plane. FIG. 9 illustrates an alternative electrode configuration where both electrodes of the impedance sensor are positioned on the same plane of a robot 910. In this example, matched electrode pairs 920, 930, and 940 are shown on a front plane of the robot 910. FIG. 10 illustrates an alternative electrode configuration where one electrode is positioned on an inner portion of a plane shown as plane (a) and another electrode is positioned on an outer portion of the plane shown as plane (b). Each electrode can be positioned over a ground plane (c) as shown.

Figure 11:
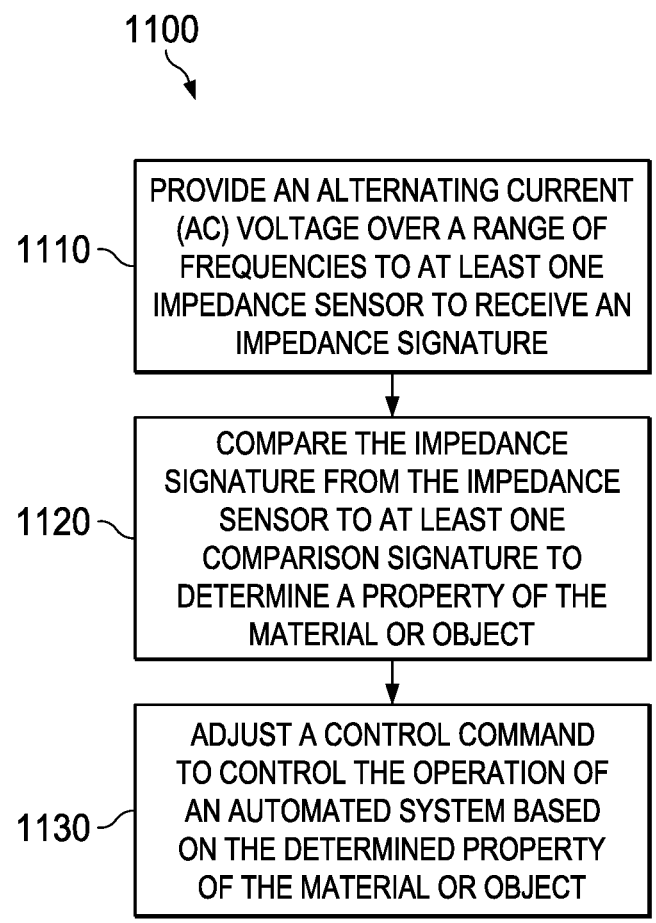
FIG. 11 illustrates a flow diagram of an example method to control automated actions based on an impedance signature that describes a property of a material or object.

In view of the foregoing structural and functional features described above, an example method will be better appreciated with reference to FIG. 11. While, for purposes of simplicity of explanation, the method is shown and described as executing serially, it is to be understood and appreciated that the method is not limited by the illustrated order, as parts of the method could occur in different orders and/or concurrently from that shown and described herein. Such method can be executed by various components configured in an integrated circuit, processor, or a controller, for example.

FIG. 11 illustrates an example method 1100 to control automated actions based on an impedance signature that describes a property of a material or object. At 1110, the method 1100 includes providing an alternating current (AC) voltage over a range of frequencies to at least one impedance sensor to receive an impedance signature that relates to a material or object in proximity to the sensor (e.g., via frequency generator 160 of FIG. 1). At 1120, the method 1100 includes comparing the impedance signature from the impedance sensor to at least one comparison signature to determine a property of the material or object (e.g., via classification logic 170 of FIG. 1). At 1130, the method 1100 includes adjusting a control command to control the operation of an automated system based on the determined property of the material or object (e.g., via signature analyzer 130 of FIG. 1). Although not shown, the method can also include analyzing at least one of a magnitude component and a phase component of the impedance signature over the range of frequencies to determine the property of the material or object.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system, comprising:
a controller to provide at least one control output to an automated system in response to a control command received at a control input of the controller, the control output controls the operation of the automated system based on the control command; and
a signature analyzer to generate the control command to the controller, the signature analyzer receives an impedance signature related to a property of a material or object encountered by the automated system, the signature analyzer compares the impedance signature to at least one comparison signature to determine the property of the material or object, the signature analyzer adjusts the control command to the controller to control the operation of the automated system based on the determined property.

2. The system of claim 1, further comprising an impedance sensor operatively coupled to the signature analyzer to generate the impedance signature, the impedance sensor includes at least two electrodes that are excited via an alternating current (AC) voltage over a range of frequencies by the signature analyzer to generate the impedance signature.

3. The system of claim 2, wherein the at least two electrodes of the impedance sensor are positioned on a similar sensing plane or on a different sensing plane with respect to each other to sense the material or object encountered by the automated system.

4. The system of claim 2, wherein the impedance signature includes at least one of a magnitude component and a phase component that is analyzed over the range of frequencies by the signature analyzer to determine the property of the material or object.

5. The system of claim 2, further comprising a vacuum robot that receives the control output from the controller in response to the control command from the signature analyzer, the vacuum robot collects material or bypasses the material based on the determined property of the material and the control command from the signature analyzer.

6. The system of claim 5, wherein the material includes solid or liquid materials that are collected or bypassed by the vacuum robot and the control command is adjusted by the signature analyzer based on a type of flooring material that is in contact with the solid or liquid materials.

7. The system of claim 2, further comprising a pick and place robot that receives the control output from the controller in response to the control command from the signature analyzer, the pick and place robot manipulates the object based on the determined property of the object and the control command from the signature analyzer.

8. The system of claim 7, wherein the determined property of the object relates to the hardness of the object and the signature analyzer adjusts to the control command to control an amount of force applied by the pick and place robot to the object.

9. The system of claim 2, further comprising an inventory selection robot that receives the control output from the controller in response to the control command from the signature analyzer, the inventory selection robot retrieves the object based on the determined property of the object and the control command from the signature analyzer.

10. The system of claim 1, further comprising at least one other sensor to detect the presence of the material or object encountered by the automated system, wherein the impedance signature is gathered from the detected object to determine if the object should be further processed or avoided by the automated system.

11. The system of claim 1, further comprising a classification logic circuit in the signature analyzer to perform the comparison, wherein the classification logic circuit includes at least one of an analog comparator, a digital comparator, or a classifier to compare the impedance signature to the comparison signature to determine the property of the material or object.

12. A circuit, comprising:
an impedance sensor that includes at least two electrodes that are excited via an alternating current (AC) voltage over a range of frequencies, the impedance sensor generates an impedance signature in relation to a material or object in proximity to the sensor;
a classification logic circuit that compares the impedance signature from the impedance sensor to at least one comparison signature to determine a property of the material or object; and
a signature analyzer processor to generate a control command to control an automated system, wherein the signature analyzer processor adjusts the control command to control the operation of the automated system based on the determined property of the material or object by the classification logic.

13. The circuit of claim 12, wherein the at least two electrodes of the impedance sensor are positioned on a similar sensing plane or on a different sensing plane with respect to each other to sense the material or object in proximity to the impedance sensor.

14. The circuit of claim 12, wherein the impedance signature includes at least one of a magnitude component and a phase component that is analyzed over the range of frequencies by the signature analyzer to determine the property of the material or object.

15. The circuit of claim 12, wherein the signature analyzer processor communicates the control command to a vacuum robot that collects material or bypasses the material based on the determined property of the material.

16. The circuit of claim 12, wherein the signature analyzer processor communicates the control command to a pick and place robot that manipulates the object based on the determined property of the object.

17. The circuit of claim 12, further comprising at least one other sensor to detect the presence of the material or object encountered by the automated system, wherein the impedance signature is gathered from the detected object via the impedance sensor to determine if the object should be further processed or avoided by the automated system.

18. The system of claim 12, wherein the classification logic circuit includes at least one of an analog comparator, a digital comparator, or a classifier to compare the impedance signature to the comparison signature to determine the property of the material or object.

19. A method, comprising:
providing an alternating current (AC) voltage over a range of frequencies to at least one impedance sensor to receive an impedance signature that relates to a material or object in proximity to the sensor;
comparing the impedance signature from the impedance sensor to at least one comparison signature to determine a property of the material or object; and
adjusting a control command to control the operation of an automated system based on the determined property of the material or object.

20. The method of claim 19, further comprising analyzing at least one of a magnitude component and a phase component of the impedance signature over the range of frequencies to determine the property of the material or object.

* * * * *